US008604027B2

(12) United States Patent
Grubb et al.

(10) Patent No.: US 8,604,027 B2
(45) Date of Patent: Dec. 10, 2013

(54) CYCLIC PROGESTIN REGIMENS AND KITS

(75) Inventors: Gary Sondermann Grubb, Newtown Square, PA (US); Ginger Dale Constantine, Malvern, PA (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 12/772,280

(22) Filed: May 3, 2010

(65) Prior Publication Data
US 2010/0292198 A1 Nov. 18, 2010

Related U.S. Application Data

(63) Continuation of application No. 11/174,592, filed on Jul. 6, 2005, now abandoned.

(60) Provisional application No. 60/586,045, filed on Jul. 7, 2004.

(51) Int. Cl.
A61K 31/535 (2006.01)
A61K 31/40 (2006.01)

(52) U.S. Cl.
USPC ........................................ 514/230.5; 514/427

(58) Field of Classification Search
USPC ........................................ 514/230.5, 427, 429
See application file for complete search history.

(56) References Cited

U.S. PATENT DOCUMENTS

| 6,407,101 | B1 | 6/2002 | Collins |
| 6,436,929 | B1 | 8/2002 | Zhang |
| 6,444,668 | B1 | 9/2002 | Grubb |
| 6,509,334 | B1 | 1/2003 | Zhang |
| 6,562,857 | B2 | 5/2003 | Collins |
| 6,566,358 | B2 | 5/2003 | Zhang et al. |
| 6,713,478 | B2 | 3/2004 | Zhang |
| 6,759,408 | B2 | 7/2004 | Grubb |
| 7,317,037 | B2 | 1/2008 | Fensome |
| 7,488,822 | B2 | 2/2009 | Zhang |
| 2003/0092711 | A1 | 5/2003 | Zhang |
| 2003/0158182 | A1 | 8/2003 | Collins |
| 2004/0186101 | A1 | 9/2004 | Zhang |
| 2005/0256110 | A1 | 11/2005 | Collins |
| 2006/0009428 | A1 | 1/2006 | Grubb |
| 2006/0009509 | A1 | 1/2006 | Grubb |
| 2006/0030615 | A1 | 2/2006 | Fensome |
| 2009/0111802 | A1 | 4/2009 | Zhang |

FOREIGN PATENT DOCUMENTS

| WO | WO-98/04269 | 2/1998 |
| WO | WO-2006/014476 | 2/2006 |

OTHER PUBLICATIONS

The ESHRE Capri Working Group. "Hormonal contraception without estrogens." Human Reproduction Update, Jul. 2003, 9(4), 373-386.*

English translation of an Office Action issued in related Chinese Patent Application No. 200580022779.6 on Sep. 17, 2010.
Applicant's Response to the Office Action issued in related Australian Patent Application No. 2005269938 on Feb. 2, 2010.
Office Action issued in related Australian Patent Application No. 2005269938 on Oct. 1, 2010.
Bapst, "Clinical Pharmacokinetics of Tanaproget, A Non-Steroidal Progesterone Receptor (PR) Agonist, in Healthy Cycling Women During 28 Days of Administration", American Society for Clinical Pharmacology and Therapeutics, Abstract PI-138, (Feb. 2005), p. 44.
Bapst, "Pharmacokinetics and Safety of Tanaproget, a Nonsteroidal Progesterone Receptor Agonist, in Healthy Women", Contraception, 74(5):414-418 (Nov. 2006; e-published Sep. 15, 2006).
Batista, "Delayed Endometrial Maturation Induced by Daily Administration of the Antiprogestin RU 486: A Potential New Contraceptive Strategy", American Journal of Obstetrics & Gynecology, 167(1):60-65 (Jul. 1992).
Brown, "Daily Low-Dose Mifepristone Has Contraceptive Potential by Suppressing Ovulation and Menstruation: A Double-Blind Randomized Control Trial of 2 and 5 mg per Day for 120 Days", Journal of Clinical Endocrinology & Metabolism, 97(1):63-70 (Jan. 2002).
Bruner-Tran "Down-Regulation of Endometrial Matrix Metalloproteinase-3 and -7 Expression in Vitro and Therapeutic Regression of Experimental Endometriosis in Vivo by a Novel Nonsteroidal Progesterone Receptor Agonist, Tanaproget", Journal of Clinical Endocrinology & Metabolism, 91(4):1554-1560 (Apr. 2006; e-published Jan. 17, 2006).
Crabtree, "Development of a Mouse Model of Mammary Gland Versus Uterus Tissue Selectivity Using Estrogen- and Progesterone-Regulated Gene Markers", Journal of Steroid Biochemistry & Molecular Biology, 101:11-21 (Sep. 2006: e-published Aug. 22, 2006).
Croxatto, "Effects of Continuous Treatment with Low Dose Mifepristone Throughout One Menstrual Cycle", Human Reproduction, 8(1):201-207 (Feb. 1993).
Croxatto, "Effects of Long-Term Low-Dose Mifepristone on Reproductive Function in Women", Human Reproduction, 13(4):793-798 (Apr. 1998).
Cullberg, "Central and Peripheral Effects of Desogestrel 15-60 μg Daily for 21 Days in Healthy Female Volunteers", Acta. Obstet. Gynecol. Scand. 61(S111):21-28 (1982).
Fensome, "Synthesis and Structure-Activity Relationship of Novel 6-Aryl-1,4-Dihydrobenzo[d][1,3]oxazine-2-thiones as Progesterone Receptor Modulators Leading to the Potent and Selective Nonsteroidal Progesterone Receptor Agonists Tanaproget", Journal of Medicinal Chemistry, 48:5092-5095 (Aug. 11, 2005).
Ledger, "Inhibition of Ovulation by Low-Dose Mifepristone (RU 486)", Human Reproduction, 7(7):945-950 (Aug. 1992).
Obruca, "Ovarian Function During and After Treatment with the New Progestagen Org 30659", Fertility and Sterility, 76(1):108-115 (Jul. 2001).
Pelissier-Langbort, "La Contraception par les progestatifs normodosés", Contraception Fertilite Sexualite, 12(10):1099-1109 (Oct. 1984).
Skouby, "Laboratory and Clinical Assessment of a New Progestational Compound, Desogestrel", Acta. Obstet. Gynecol. Scand. 61(S111):7-11, (1982).

(Continued)

Primary Examiner — Paul Zarek
(74) Attorney, Agent, or Firm — Howson & Howson LLP

(57) ABSTRACT

A method of contraception is provided which involves delivery of 21 to 27 consecutive days of a progestin in the absence of an estrogen or other steroidal compound, followed by 1 to 7 days without an effective amount of an active agent. Also described is a pharmaceutically useful kit to facilitate delivery of this regimen.

18 Claims, No Drawings

(56) References Cited

OTHER PUBLICATIONS

Spitz, "Progesterone Antagonists and Progesterone Receptor Modulators: an Overview", Fertility & Sterility, 59(5):971-975 (May 1993).

Winneker, "A New Generation of Progesterone Receptor Modulators" Steroids, 73(7):689-701 (Jul. 2008).

Zhang, "Molecular and Pharmacological Properties of a Potent and Selective Novel Nonsteroidal Progesterone Receptor Agonist Tanaproget", Journal of Biological Chemistry, 280(31:28468-28475 (Aug. 5, 2005).

The Eshre Capri Working Group, "Hormonal Contraception Without Estrogens", Human Reproduction Update, 9(4):373-386 (Jul./Aug. 2003).

Wyeth, "Wyeth reviews R&D pipeline", retrieved from the Internet on Mar. 9, 2010 from http://integrity.prous.com (Jun. 7, 2004).

International Search Report dated Nov. 24, 2005 and issued by the searching authority in related International Patent Application No. PCT/US2005/023955.

Office Action dated Mar. 12, 2009 and issued in parent U.S. Appl. No. 11/174,592.

Applicants' Response to the Office Action dated Mar. 12, 2009 and issued in parent U.S. Appl. No. 11/174,592.

Office Action dated Nov. 5, 2009 and issued in parent U.S. Appl. No. 11/174,592.

Office Action dated Jan. 23, 2009 and issued in related Chinese patent Application No. 200580022779.6.

Office Action dated Nov. 20, 2009 and issued in related Chinese Patent Application No. 200580022779.6.

Office Action dated Mar. 17, 2010 and issued in related European Patent Application No. 200580022779.6.

Office Action dated Feb. 2, 2010 and issued in Australian Patent Application No. 2005269938.

"WHO Drug Information", vol. 18, No. 1, Jun. 1, 2004.

Office Action dated Jun. 30, 2011 and issued in Chinese Patent Application No. 200580022779.6.

Office Action dated Mar. 1, 2013 and issued in Chinese Patent Application No. 200580022779.6.

Office Action dated Sep. 6, 2011 and issued in Japanese Patent Application No. 2007-520464.

Office Action dated Jun. 12, 2012 and issued in Japanese Patent Application No. 2007-520464.

Correspondence from the foreign agent dated Jun. 7, 2012 regarding the issuance of an Office Action in Mexican Patent Application No. PA/a/2006/014579.

Correspondence from the foreign agent dated Sep. 24, 2012 regarding the issuance of an Office Action in Mexican Patent Application No. PA/a/2006/014579.

Office Action dated Jul. 23, 2012 and issued in Indian Patent Application No. 305/DELNP/2007.

Office Action dated Feb. 29, 2012 and issued in Canadian Patent Application No. 2,571,377.

Applicant's Response to the Office Action dated Feb. 29, 2012 and issued in Canadian Patent Application No. 2,571,377.

Applicant's Response to the Office Action dated Mar. 17, 2010 and issued in European Patent Application No. 05768415.1.

Office Action dated Aug. 4, 2011 and issued in European Patent Application No. 05768415.1.

Applicant's Response to the Office Action dated Aug. 4, 2011 and issued in European Patent Application No. 05768415.1.

Office Action dated Dec. 21, 2012 and issued in Australian Patent Application No. 2011244870.

Bray, "Quantitative analysis of gene regulation by seven clinically relevant progestins suggests a highly similar mechanism of action through progesterone receptors in T47D breast cancer cells", J. Steroid Biochem. Mol. Biol. 97:328-341 (Dec. 2005; e-publication: Sep. 12, 2005).

Winneker, "The preclinical biology of a new potent and selective progestin: trimegestone", Steroids, 68: 915-920 (Nov. 2003).

Stanczyk, "All progestins are not created equal", Steroids, 68: 879-890 (Nov. 2003).

Phillips, "Progestational and androgenic receptor binding affinities and in vivo activities of norgestimate and other progestins", Contraception, 41(4):399-410 (Apr. 1990).

* cited by examiner

SEQUENCE LISTING

<160> NUMBER OF SEQ ID NOS: 3

<210> SEQ ID NO 1
<211> LENGTH: 25
<212> TYPE: DNA
<213> ORGANISM: Artificial Sequence
<220> FEATURE:
<223> OTHER INFORMATION: C3 specific primer

<400> SEQUENCE: 1
ggtcggtcaa ggtctactcc tacta                25

<210> SEQ ID NO 2
<211> LENGTH: 20
<212> TYPE: DNA
<213> ORGANISM: Artificial Sequence
<220> FEATURE:
<223> OTHER INFORMATION: C3 specific primer

```
<400> SEQUENCE: 2
cacagcggca catttcattg                                            20

<210> SEQ ID NO 3
<211> LENGTH: 26
<212> TYPE: DNA
<213> ORGANISM: Artificial Sequence
<220> FEATURE:
<223> OTHER INFORMATION: customized probe

<400> SEQUENCE: 3
agcattccat cgtccttctc cggatg                                     26
```

CYCLIC PROGESTIN REGIMENS AND KITS

CROSS-REFERENCE TO RELATED APPLICATIONS

This application is a continuation of U.S. patent application Ser. No. 11/174,592, filed Jul. 6, 2005, which claims the benefit of the priority under 35 USC 119(e) of U.S. Provisional Patent Application No. 60/586,045, filed Jul. 7, 2004, now expired. These priority applications are herein incorporated by reference.

BACKGROUND OF THE INVENTION

Soon after the introduction of progestin/estrogen combination oral contraceptives (OCs) pills in 1960, several progestin-only pills (POPS) were introduced. The dose of the progestin in the POPs was made lower than in the combined OCs to minimize the occurrence of amenorrhea resulting from complete ovarian suppression. Consequently, ovulation was inhibited in about half the users of POPs. (The standard POPs primarily depend upon cervical mucus thickening to provide contraceptive protection for those who ovulate). Partly because of the lower progestin dose, the absence of exogenous estrogen and the absence of regular withdrawal bleed, POP users have a much higher rate of unscheduled breakthrough bleeding and spotting than combination OC users. Primarily because of the bleeding problems, POPs are used by only about 1-2% of contracepting women, compared to about 30% using combination OCs.

What is needed is a progestin-containing contraceptive which avoids breakthrough bleeding and spotting problems.

SUMMARY OF THE INVENTION

The present invention provides a contraceptive regimen which involves delivery of an effective amount of a progestin for 21 to 27 consecutive days followed by 1 to 7 consecutive days without delivery of same. In one embodiment, the progestin is 5-(4,4-Dimethyl-2-thioxo-1,4-dihydro-2H-benzo[d][1,3]oxazin-6-yl)-1-methyl-1H-pyrrole-2-carbonitrile, also termed tanaproget.

The invention further provides a pharmaceutical kit for use in delivery of the regimen.

Other aspects of the invention will be readily apparent from the following detailed description of the invention.

DETAILED DESCRIPTION OF THE INVENTION

In one aspect, the present invention provides a method of contraception in a female of child-bearing age. In this method, a progestin, or combination of progestins, is delivered for a period of consecutive days as the sole active (i.e., anti-contraceptive) agent in order to prevent conception.

In another aspect, the present invention provides for the use of a progestin, or combination of progestins, in preparing a medicament useful for contraception in a female of child-bearing age. In one embodiment, the medicament comprises one phase in which, from 21 to 27 daily dosage units are consecutively administered, each containing an active agent comprising a progestin. In a further embodiment, the medicament also comprises from 1 to 7 daily dosage units of a pharmaceutically acceptable placebo for administration in a second phase. In other embodiments, progestins are useful in preparing medicaments useful in any of the methods of contraception described herein.

Without wishing to be bound by theory, it is believed that this invention will reduce the bleeding problems of conventional progestin-only contraceptives in two ways. First, due to the incorporation of 1 to 7 days in each cycle with no effective amount of a progestin, a regular withdrawal bleed will occur approximately every 28 days. Second, increasing the progestin dose above standard progestin-only contraceptives produces almost complete ovulation inhibition and the composition of the invention does not depend on cervical mucus thickening to maintain the contraceptive effectiveness as do conventional progestin-only regimens.

The term "progestin," as used herein, refers to any progestationally active compound, i.e., any compound that binds to and activates the progesterone receptor. Representative progestins include progesterone synthetic derivatives such as, for example, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, dl-norgestrel, d-17α-acetoxy-13β-ethyl-17α-α-ethinyl-gon-4-en-3-one oxime, cyproterone acetate, gestodene, desogestrel, etonorgestrel, norgestimate and norelgestromin. Other compounds with progestational activity used in oral contraceptives include chlormadione, dienogest, and drospirenone.

In one embodiment, the progestin is 5-(4,4-dimethyl-2-thioxo-1,4-dihydro-2H-benzo[d][1,3]oxazin-6-yl)-1-methyl-1H-pyrrole-2-carbonitrile, also termed tanaproget and NSP-989. This compound can have the formula:

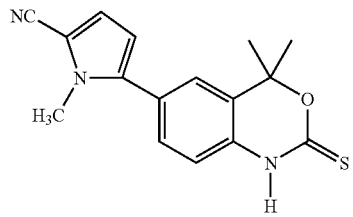

and encompasses pharmaceutically acceptable salts, esters or other prodrug forms thereof. This compound and methods of making same are described in U.S. Pat. No. 6,436,929, U.S. patent application Ser. No. 11/113,794 (filed Apr. 25, 2005), and U.S. Provisional Patent Application Nos. 60/675,550 (filed Apr. 28, 2005); 60/675,551 (filed Apr. 28, 2005); 60/675,559 (filed Apr. 28, 2005); 60/675,737 (filed Apr. 28, 2005); and 60/675,738 (filed Apr. 28, 2005).

In addition, other progestins described in U.S. Pat. Nos. 6,436,929; 6,355,648; 6,521,657; 6,407,101; 6,562,857; and 6,358,947, US Patent Publication No. 2003-0158182, and U.S. Provisional Patent Application No. 60/601,254 (filed Aug. 13, 2004) may be useful in the methods and kits of the invention.

The progestin compounds useful in the present invention can be used in the form of salts derived from pharmaceutically or physiologically acceptable acids or bases. These salts include, but are not limited to, the following salts with inorganic acids such as hydrochloric acid, sulfuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium in the form of esters, carbamates and other conventional "pro-drug" forms, which, when administered in such form, convert to the active moiety in vivo.

The method of the invention is performed for a period of time corresponding to the length of a menstrual cycle, i.e., in the range of 23 to 35 days, with 28 days being the average. Thus, the method of the invention involves delivering a daily dosage unit containing an effective amount of an active agent consisting of a progestin to a female of child bearing age over a period of 18 to 28 consecutive days followed by 1 to 7 consecutive days in which no effective amount of an active agent is delivered to the subject.

The term "effective amount" of a progestin(s) is a dosage that provides contraception. Without being bound by theory, this is achieved primarily by preventing ovulation. The term "no effective amount" of a progestin(s) is used to refer to the 1 to 7 days following delivery of an effective amount of the progestin(s). During this period, preferably, no amount of a progestin(s) is delivered to the animal. However, it is possible, that a sustained release formulation or other delivery method may be "leaky" and continue to deliver low amounts of a progestin which are not effective at contraception during this period. The phrase "no effective amount" encompasses delivery of no amount of progestin(s).

According to the present invention, a female is preferably a human. However, as used herein, a female can include non-human mammals, e.g., cattle or livestock, horses, pigs, domestic animals, etc.

In one aspect, the method of invention involves delivering a daily dosage unit containing an active agent consecutively for at least 21 of 28 consecutive days. In the embodiment, the regimen consists of delivering a progestin to a female of child bearing age over a period of 21 to 27 consecutive days followed by 1 to 7 consecutive days in which no effective amount or no amount of active agent is delivered to the subject. Optionally, the period of 1 to 7 days in which no effective amount of an active agent is delivered to the subject can involve delivery of a second phase of daily dosage units of 1 to 7 days of a pharmaceutically acceptable placebo. Alternatively, during this "placebo period", no placebo is administered.

In one embodiment, the method of the invention involves delivering a progestin as the sole active agent for 21 consecutive days followed by 7 days in which no effective amount of an active agent is delivered. Optionally, during these 7 days, a second phase of 7 daily dosage units of an orally and pharmaceutically acceptable placebo can be delivered.

In another embodiment, the method of the invention involves delivering a progestin as the sole active agent for 23 consecutive days followed by 5 days in which no effective amount of an active agent is delivered. Optionally, during these 5 days, a second phase of 5 daily dosage units of an orally and pharmaceutically acceptable placebo can be delivered.

In still another embodiment, the method of the invention involves delivering a progestin as the sole active agent for 25 consecutive days followed by 3 days in which no effective amount of an active agent is delivered. Optionally, during these 3 days, a second phase of 3 daily dosage units of an orally and pharmaceutically acceptable placebo can be delivered.

In still another embodiment, the method of the invention involves delivering a progestin as the sole active agent for 27 consecutive days followed by 1 day in which no effective amount of an active agent is delivered. Optionally, a second phase of 1 daily dosage unit of an orally and pharmaceutically acceptable placebo can be delivered.

This invention includes the use of pharmaceutical compositions containing one or more progestin compound(s) as the sole active ingredient in the formulation and regimen. The progestin compounds are formulated with a pharmaceutically acceptable carrier or excipient.

Suitably, the progestins used in the invention are formulated for delivery by any suitable route including, e.g., transdermal, mucosal (intranasal, buccal, vaginal), oral, parenteral, etc, by any suitable delivery device including, e.g., transdermal patches, topical creams or gels, a vaginal ring, among others. In a further embodiment, the progestins are delivered by any suitable route in a sustained release formulation. Such sustained release formulations are known to those of skill in the art.

When the compounds are employed for the above utilities, they may be combined with one or more pharmaceutically acceptable carriers or excipients, for example, solvents, diluents and the like. When formulated for oral delivery, the progestin compound can be in the form of a tablet, capsule, caplet, gel tab, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like. When formulated for parenteral delivery, the compositions can be delivered in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredient employed may vary depending on the particular compound employed, the mode of administration and the degree of ovarian suppression desired. However, in general, satisfactory results are obtained when the compounds of the invention are administered at a daily dosage of from about 0.03 to 0.6 mg, or about 0.1 to about 0.5 mg, preferably given daily or in a sustained release form. This dosage regimen may be adjusted to provide the optimal therapeutic response. For example, several divided doses may be administered daily or the dose may be proportionally reduced as indicated by the exigencies of the therapeutic situation.

These active compounds (one or more progestins) may be administered orally. Solid carriers include starch, lactose, dicalcium phosphate, microcrystalline cellulose, sucrose and kaolin, while liquid carriers include sterile water, non-ionic surfactants, ethanol (e.g., glycerol, propylene glycol and liquid polyethylene glycols), suitable mixtures thereof, and vegetable or edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered via a vaginal ring. Suitably, use of the vaginal ring is timed to the 28 day cycle. In one embodiment, the ring is inserted into the vagina, and it remains in place for 3 weeks. During the fourth week, the vaginal ring is removed and menses occurs. The following week a new ring is inserted to be worn another 3 weeks until it is time for the next period. In another embodiment, the vaginal ring is inserted weekly, and is replaced for three consecutive weeks. Then, following one week without the ring, a new ring is inserted to begin a new regimen. In yet another embodiment, the vaginal ring is inserted for longer or shorter periods of time.

For use in the vaginal ring, a progestin compound is formulated in a manner similar to that described for contraceptive compounds previously described for delivery via a vaginal ring. See, e.g., U.S. Pat. Nos. 5,972,372; 6,126,958; and 6,125,850.

Optionally, a progestin composition can be formulated for parenteral delivery in a sustained release formulation and administered by injection, e.g., monthly or quarterly.

In another aspect of the invention, a progestin compound is formulated for delivery via a cream or a gel, by a suitable route. Suitably, carriers for such routes are known to those of skill in the art.

In still another aspect of the invention, the progestin compound(s) are delivered via a transdermal patch. Suitably, use of the patch is timed to the 28 day cycle. In one embodiment, the patch is applied via a suitable adhesive on the skin, where it remains in place for 1 week and is replaced weekly for a total period of three weeks. During the fourth week, no patch is applied and menses occurs. The following week a new patch is applied to be worn to begin a new regimen. In yet another embodiment, the patch remains in place for longer, or shorter periods of time.

This invention also includes kits or packages of pharmaceutical formulations designed for use in the regimens described herein. Suitably, the kits contain one or more progestin compounds as described herein. In one embodiment, the progestin is selected from among 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, di-norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione, dienogest, and drospirenone. In addition, other progestins described in U.S. Pat. Nos. 6,436,929; 6,355,648; 6,521,657; 6,407,101; and 6,562,857, may be useful in the methods and kits of the invention.

In one desirable embodiment, the progestin is NSP-989, also termed tanaproget, or a pharmaceutically acceptable salt or prodrug thereof.

Advantageously, for use in the kits of the invention, the progestin is formulated for the desired delivery vehicle and route. For example, a progestin can be formulated for oral delivery, parenteral delivery, vaginal ring, transdermal delivery, or mucosal delivery.

In one embodiment, the kit of the invention is designed for daily oral administration over a 28-day cycle, preferably for one oral administration per day, and organized so as to indicate a single oral formulation or combination of oral formulations to be taken on each day of the 28-day cycle. Preferably each kit will include oral tablets to be taken on each the days specified; preferably one oral tablet will contain each of the combined daily dosages indicated. For example, a kit of the invention can contain 21 to 27 daily dosage units of an effective amount of an active agent and, optionally, 1 to 7 daily dosage units of a placebo and other appropriate components including, e.g., instructions for use.

The kit of the invention is preferably a pack (e.g., a blister pack) containing daily doses arranged in the order in which they are to be taken.

In another embodiment, the kit of the invention is designed for weekly or monthly administration via a vaginal ring over a 28-day cycle. Suitably, such a kit contains individual packaging for each of the vaginal rings, i.e., one to three, required for a monthly cycle and other appropriate components, including, e.g., instructions for use.

In another embodiment, the kit of the invention is designed for weekly or monthly administration via a transdermal patch over a 28-day cycle. Suitably, such a kit contains individual packaging for each of the patches, i.e., one to three, required for a monthly cycle and other appropriate components including, e.g., instructions for use.

In still another embodiment, the kit of the invention is designed for parenteral delivery of the progestin. Such a kit is typically designed for delivery at home and may include needles, syringes, and other appropriate packaging and instructions for use.

In yet another embodiment, the kit of the invention contains a progestin compound in a gel or cream formulation. Optionally, the kit can include appropriate packaging such as a tube or other container, an applicator, and/or instructions for use.

In each of the regimens and kits described herein, it is preferred that the daily dosage of each pharmaceutically active component of the regimen remain fixed in each particular phase in which it is administered. It is also understood that the daily dose units described are to be administered in the order described, with the first phase followed in order by the optional second phase. To help facilitate compliance with each regimen, it is also preferred that the kits contain the placebo described for the final days of the cycle. It is further preferred that each package or kit comprise a pharmaceutically acceptable package having indicators for each day of the 28-day cycle, such as a labeled blister package, dial dispenser, or other packages known in the art.

These dosage regimens may be adjusted to provide the optimal contraceptive effect. For example, several divided doses of each component may be administered daily or the dose may be proportionally increased or reduced as indicated by the contraceptive effectiveness. In the descriptions herein, reference to a daily dosage unit may also include divided units which are administered over the course of each day of the cycle contemplated.

The following examples are illustrative only and are not intended to be a limitation on the present invention.

EXAMPLE 1

Ovulation Inhibition by the Progestin Compound NSP-989

The activity of NSP-989 was evaluated orally in three 3 different rat models for progestin activity along with reference progestins medroxyprogesterone acetate (MPA) and trimegestone (TMG) in 2% Tween 80/0.5% methylcellulose vehicle. These models are described in Parts A, B and C of this example.

A. Effect of NSP-989 in the Rat Ovulation Inhibition Model

The ovulation inhibition assay measures a compound's ability to inhibit ovulation in adult female rats. This activity is essential for contraceptive efficacy. In this assay, NSP-989 had a mean $ED_{100}$ value of 0.03 mg/kg, whereas both TMG and MPA had $ED_{100}$ values of 1 mg/kg (n=2- to 3).

Random cycling mature female Sprague-Dawley rats (~200 g) were obtained from Charles River Laboratory (Boston, Mass.). Rats were synchronized for estrus with 2 µg of LHRH (in phosphate buffered saline containing 0.1% bovine serum albumin) administered subcutaneously (sc) per rat at 0900 h and again at 1600 h. Animals were allowed to rest for 8 days before the administration of test compounds. Animals were then grouped, with 7 to 9 rats per treatment group. The morning of the ninth day following LHRH treatment, the rats were treated with test compounds once daily, by gavage. This continued for 4 consecutive days. The animals were euthanized the morning following the last treatment. Oviducts were removed, placed between 2 glass slides, and viewed through a dissecting microscope to count ova. The number of animals presenting ova in the oviduct from each treatment group and the number of ova in the oviduct of each animal were recorded.

B. Rat Decidualization Model

The second rat model to determine progestational activity is the uterine decidualization assay in adult ovariectomized rats. Only compounds that are progesterone receptor agonists will be active in this model, as a progestin is absolutely required to transform uterine stromal cells to differentiated decidual cells.

Rat decidualization assay was run as described previously [Lundeen S G, et al., "Rat uterine complement C3 expression as a model for progesterone receptor modulators: characterization of the new progestin trimegestone", J Steroid Biol Mol. Biol. 2001; 78:137-143.]

Briefly, mature female Sprague-Dawley rats (~220 g) were ovariectomized at least 10 days prior to treatment to reduce circulating sex steroids. NSP-989 was administered once daily for seven 7 days orally by gavage (0.5 ml) in 2% Tween 80/0.5% methyl-cellulose vehicle. Approximately 24 hours after the third daily treatment, decidualization was induced in one uterine horn of each anesthetized rat by scratching the antimesometrial luminal epithelium with a blunt 21-gauge needle. The contralateral horn was not scratched and served as a non-stimulated control. Animals were euthanized by $CO_2$ asphyxiation 24 hours following the final treatment. The uteri were removed, and trimmed of fat, and the decidualized (D) and control (C) horns were weighed separately. The decidual response is expressed as D/C.

NSP-989 induced endometrial decidualization with an $ED_{50}$ value of 0.01 mg/kg (n=23) and was approximately 40- and 100-fold more potent than MPA and TMG, respectively (Table 1).

TABLE 1

Summary of Progestational Activity of NSP-989 in Various Rodent Models

| Compound | Rat Ovulation Inhibition Assay $ED_{100}$ (mg/kg, po) | Rat Decidual Assay $ED_{50}$ (mg/kg, po) | Rat C3 Assay $ED_{50}$ (mg/kg, po) | Rabbit Clauberg Assay $AED_{50}$ (mg/kg, po) |
|---|---|---|---|---|
| NSP-989 | 0.03 | 0.01 | 0.0005 | 0.001 |
| MPA | 1.0 | 0.4 | 0.03 | 0.03 |
| TMG | 1.0 | 1.0 | 0.005 | 0.001 |

C. Rat Uterine C3 Model

The third model for PR agonist activity was the adult ovariectomized rat uterine C3 model. This assay evaluates the ability of a progestin to block estrogen-induced C3 expression in the uterine epithelium.

Ovariectomized female, 60 day-old Sprague-Dawley rats were obtained from Harlan (Indianapolis, Ind.). Ovariectomies were performed by the supplier a minimum of 8 days prior tobefore treatment. The rats were randomized and placed in groups of 6. The animals were treated once daily for (2) two days orally by gavage (p.o.) in a volume of 0.5 mL. On the second day of treatment, the animals were also treated with EE (0.08 mg/kg body weight (BW)) orally by gavage. Approximately 24 hours after the final treatment, the animals were euthanized by $CO_2$ asphyxiation. The uteri were then removed, stripped of remaining fat and mesentery, weighed, and snap-frozen on dry ice. Total RNA was isolated from the uteri using the Trizol Reagent (GibcoBRL) as described by the manufacturer. Real-time reverse transcription polymerase chain reaction (RT-PCR) as previously reported [Sampath D, et al., "Aberrant expression of Cyr61, a member of the CCN (CTGF/Cyr61/Cef10/NOVH) family, and dysregulation by 17b-estradiol and basic fibroblast growth factor in human uterine leiomyomas" *J Clin Endocrinol Metab* 2001; 86:1707-1715] was used to quantitate complement C3 expression. Briefly, RNA samples were DNAse-I treated using a DNA-free kit (Ambion). A total of 50 ng of RNA was analyzed in triplicate using C3 specific primer pair (5' primer GGTCGGTCAAGGTCTACTCCTACTA [SEQ ID NO: 1], 3' primer CACAGCGGCACATTTCATTG [SEQ ID NO: 2]) and customized probe (6FAM-AGCATTCCATCGTCCT-TCTCCGGATG-TAMRA [SEQ ID NO: 3]). C3 messenger RNA (mRNA) levels were normalized to 18s 18S ribosomal RNA contained within each sample reaction using primers and probe supplied by PE Applied Biosystems.

The mean $ED_{50}$ value for NSP-989 was 0.0005 mg/kg (n=6). Both MPA and TMG had mean $ED_{50}$ values of 0.03 and 0.005 mg/kg, respectively in this assay. In summary, in the rats, in several unrelated models for progestin activity, NSP-989 was 3010- to 10060-fold more potent than the reference progestins used in these studies.

D. Rabbit Endometrial Transformation (Clauberg) Assay

In addition to the rat progestational models described above, NSP-989 was also evaluated in the Clauberg model, a classic progestational assay in the rabbit endometrial transformation model [McPhail MK, "The assay of progestin." *J Physiol* 1934; 83:145-1567]. Briefly, immature female New Zealand White rabbits (~1 kg body weight) were injected subcutaneously with 5 µg 17ß-estradiol ($E_2$)/rabbit/day for six consecutive days. Beginning 24 hours after the final $E_2$ injection, vehicle alone or test compounds were given orally for (5) five consecutive days. Progestational activity was determined by increases in uterine weight and endometrial glandular arborization (McPhail Index).

In limited dose response studies, NSP-989 had an estimated $ED_{50}$ ($AED_{50}$) of 0.001 mg/kg. Its potency in this assay was similar to TMG and about 30-fold more potent than MPA.

EXAMPLE 2

Cyclic Regimen Using Progestin Compound

A phase 2, randomized, double-blind, multicenter, dose-ranging study of 3 doses of NSP-989 in a 21-day regimen followed by 7 days of placebo pills, and a comparator (the combination steroidal OC desogestrel (DSG) 150 µg/20 µg ethinyl estradiol for 21 days followed by 2 days of placebo pills, followed by 5 days of 10 µg EE, marketed in the United States under the name Mircette) is planned.

Approximately 20 sites will participate with approximately 16 subjects per site. However, the enrollment will be competitive, and additional subjects can be enrolled at any site.

The study will have 2 parts. Part 1 (days 1-84) of the study will evaluate the ability of NSP-989 to produce ovarian suppression, along with evaluating cycle control, side effects, and metabolic data. Part 2 (days 85-168) will continue to follow the subjects to collect cycle control, side effects, and metabolic data. The study will be monitored routinely by the blinded project medical monitor and study team for efficacy failures and safety Each subject will participate for up to 9 months, depending on the length of the subject's screening period. Eight (8) cycles will be observed. The first cycle will be a baseline observation of ovulation. Six (6) treatment cycles will be followed by 1 posttreatment observation cycle to assess return to ovulation. The subjects will be healthy women of 18 years of age who are younger than 36 years at the time of randomization. Subjects must have had spontaneous regular (24- to 32-day) menstrual cycles for the 3-month period preceding entry into the pretreatment observation cycle, excluding postabortal and nonbreastfeeding postpartum subjects. Postabortal and nonbreastfeeding postpartum subjects must have completed at least 1 regular (24- to 32-day) spontaneous menstrual cycle before entry into the pretreatment observation cycle. The pretreatment observation cycle for all subjects will begin on day 1 of the subsequent spontaneous menses after completion of the prestudy screening (visit 1).

The pretreatment observation cycle is a control cycle; no test article will be administered. Each subject will begin test article on the first day of her menstrual bleeding (first subject pack only). Each subject pack will contain NSP-989 or the steroid combination OC comparator. Subjects will take NSP-989 orally, once daily for 21 days (days 1 through 21), followed by 7 days of placebo pills (days 22 through 28) for 6 cycles. Subjects assigned to a steroid combination OC comparator, DSG 150 µg, will take test article orally, once daily for 21 days (days 1 through 21), followed by 2 days of placebo pills (days 22 through 23), followed by 5 days of 10 µg EE (days 24 through 28) for 6 cycles. There will also be a posttreatment cycle in which no test article will be administered and return to ovulation will be assessed.

Each subject will be randomly assigned to receive one of the following:

| Group | Treatment |
|---|---|
| A | 100 µg of NSP-989 for 21 days followed by 7 days of placebo pills |
| B | 200 µg of NSP-989 for 21 days followed by 7 days of placebo pills |
| C | 300 µg of NSP-989 for 21 days followed by 7 days of placebo pills |
| D | Desogestrel 150 µg for 21 days followed by 2 days of placebo pills, followed by 5 days of 10 µg EE |

Each subject will begin test article on the first day of her menstrual bleeding (first subject pack only). Subjects will take test article orally, once daily for 28 days, at approximately the same time each day. All subsequent subject packs will begin following day 28 of the previous pill pack. Subjects will take test article daily without interruption during the treatment cycles.

It is anticipated that one or more treatment groups A, B and C receiving a regimen of the invention will have experience effective contraception, cessation of ovulation, and all groups will have a withdrawal bleed during the fourth week of each month of treatment.

EXAMPLE 3

A blister pack with 28 blister containers is made with a cardboard, paperboard, foil or plastic backing and enclosed in a suitable cover. The blister containers are arranged to house a sequence of 21 pills each providing a daily dose of 100 µg of NSP-989 followed by 7 daily doses of placebo pills (or 7 empty blisters). Each blister container may conveniently be numbered or otherwise marked, e.g., starting with the first of the 21 dosage units that contain the active ingredient followed by 7 empty blisters or by 7 dosage units that contain no active agent.

All patents, patent publications, and other publications listed in this specification, and the sequence listing, are incorporated herein by reference. While the invention has been described with reference to particular embodiments, it will be appreciated that modifications can be made without departing from the spirit of the invention. Such modifications are intended to fall within the scope of the appended claims.

We claim:

1. A method of contraception in a female of child bearing age which comprises administering over a period of 28 consecutive days:
   (a) a first phase in which from 21 to 27 daily dosage units of an active agent are administered, each daily dosage unit containing an effective amount of an active agent consisting of a progestin of the formula:

[chemical structure]

(b) a second phase of from 1 to 7 days wherein no effective amount of said progestin is administered;
   wherein said method is performed in the absence of a second steroidal compound.

2. The method according to claim 1, wherein from 1 to 7 daily dosage units of a pharmaceutically acceptable placebo are delivered in the second phase.

3. The method according to claim 1, which comprises:
   a) a first phase of 21 daily dosage units; and
   b) a second phase of 7 daily dosage units of an orally and pharmaceutically acceptable placebo.

4. The method according to claim 1, which comprises:
   a) a first phase of 23 daily dosage units; and
   b) a second phase of 5 daily dosage units of an orally and pharmaceutically acceptable placebo.

5. The method according to claim 1, which comprises:
   a) a first phase of 25 daily dosage units; and
   b) a second phase of 3 daily dosage units of an orally and pharmaceutically acceptable placebo.

6. The method according to claim 1, which comprises:
   a) a first phase of 27 daily dosage units; and
   b) a second phase of 1 daily dosage units of an orally and pharmaceutically acceptable placebo.

7. The method according to claim 1, wherein said effective amount is between about 0.03 and about 0.6 mg.

8. The method according to claim 7, wherein said effective amount is between about 0.1 and about 0.5 mg.

9. The method according to claim 8, wherein said effective amount is about 0.1 mg.

10. The method according to claim 8, wherein said effective amount is about 0.2 mg.

11. The method according to claim 8, wherein said effective amount is about 0.3 mg.

12. The method according to claim 1, which produces complete ovulation inhibition in said female.

13. The method according to claim 1, which does not rely on cervical mucus thickening of said female.

14. A method of contraception in a female of child bearing age, said method comprising administering over a period of 28 consecutive days:
   (a) a first phase in which from 21 to 27 daily dosage units of an active agent are administered, each daily dosage unit containing an effective amount of an active agent consisting of a progestin of the formula:

[chemical structure]

(b) a second phase of from 1 to 7 days wherein no effective amount of said progestin is administered;
   wherein said method is performed in the absence of an estrogen.

15. A method of contraception in a female of child bearing age which consists essentially of administering over a period of 28 consecutive days:
   (a) a first phase in which from 21 to 27 daily dosage units of an active agent are administered, each daily dosage unit consisting of an effective amount of Tanaproget;
   (b) a second phase of from 1 to 7 days wherein no effective amount of Tanaproget is administered;
   wherein said method is performed in the absence of a second steroidal compound.

16. A method of contraception in a female of child bearing age which consists essentially of administering over a period of 28 consecutive days:
   (a) a first phase in which from 21 to 27 daily dosage units of an active agent are administered, each daily dosage unit consisting of an effective amount of Tanaproget;
   (b) a second phase of from 1 to 7 days wherein no effective amount of Tanaproget is administered;

wherein said method is performed in the absence of an estrogen.

17. A method of contraception in a female of child bearing age which consists of administering over a period of 28 consecutive days:
   (a) a first phase in which from 21 to 27 daily dosage units of an active agent are administered, each daily dosage unit consisting of an effective amount of an active agent consisting of Tanaproget;
   (b) a second phase of from 1 to 7 days wherein no effective amount of Tanaproget is administered;
   wherein said method is performed in the absence of a second steroidal compound.

18. A method of contraception in a female of child bearing age which consists of administering over a period of 28 consecutive days:
   (a) a first phase in which from 21 to 27 daily dosage units of an active agent are administered, each daily dosage unit consisting of an effective amount of an active agent consisting of Tanaproget;
   (b) a second phase of from 1 to 7 days wherein no effective amount of Tanaproget is administered;
   wherein said method is performed in the absence of an estrogen.

* * * * *